(12) United States Patent
Noda et al.

(10) Patent No.: US 6,310,242 B1
(45) Date of Patent: Oct. 30, 2001

(54) PROCESS FOR PREPARING D-ALLOISOLEUCINE AND INTERMEDIATES FOR PREPARATION

(75) Inventors: Hirofumi Noda; Koji Ohsaka; Kenichi Sakai; Hisamichi Murakami, all of Tokyo (JP)

(73) Assignee: Yamakawa Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 09/251,475

(22) Filed: Feb. 17, 1999

(30) Foreign Application Priority Data

Feb. 20, 1998 (JP) .................................................. 10-039365
May 12, 1998 (JP) .................................................. 10-129339

(51) Int. Cl.[7] ...................... C07C 205/00; C07C 207/00; C07C 229/00
(52) U.S. Cl. ........................... 562/553; 562/554; 562/575
(58) Field of Search .................................... 562/553, 554, 562/575

(56) References Cited

FOREIGN PATENT DOCUMENTS 704983   3/1954   (GB) .

OTHER PUBLICATIONS

Handbook of Chemistry and Physics, 52nd Edition (1971–1972) p. C355.*
Kaneko, T; "Amino Acid Industry, Synthesis and Utilization", *Kodansha Scientific*, p. 133, (1973).
Huffman, W.A. Hooper et al., "The Resolution of Amino Acids. II. Isoleucine . . . ", *J.Am. Chem. Soc.*, 73, p. 3366, (1951).
Flouret, George et al., "On a Convenient Resolution Method for the Preparation . . . ", *J. Org. Chem.*, vol. 40, No. 18, p. 2635 (1975).
Lloyd–Williams, Paul et al., "Synthesis of D–Alloisoleucine from L–Isoleucine . . . ", *J. Chem. Soc. Perkin Trans.*, vol. I, p. 1969, (1994).
Langenbeck, Wolfgan et al., "Racemat–Spaltung . . . ", *Chem. Ber.*, vol. 86, p. 1524, (1953).

Kearley, F.J. et al., "The Resolution of Amino Acids. IV. Lysine", *J. Am. Chem. Soc.*, vol. 73, p. 5783, (Dec. 1951).
Fogassy, E. et al., "The Problems of the Optical Resolution of Asparagine . . . ", *Period. Polytech. Chem. Eng.*, vol. 20, p. 179, (1976).
Chibata, I. et al. "Resolution and Racemization of Amino Acids", *Chemical Review*, No. 4, Chapter 9, pp. 233, (1974).

* cited by examiner

*Primary Examiner*—Johann Richter
*Assistant Examiner*—Sikarl A. Witherspoon
(74) *Attorney, Agent, or Firm*—Kubovcik & Kubovcik

(57) ABSTRACT

Disclosed are a novel process for preparing D-alloisoleucine and an improved process for epimerizing L-isoleucine to prepare D-alloisoleucine. In the former process, (2S, 3S)-tartaric acid derivative of formula I below; wherein R stands for a hydrogen atom, a $C_1$–$C_3$ lower alkyl group, lower alkoxy group, chlorine atom, bromine atom and nitro group; and "n" is a number of 0, 1 and 2; is combined with an epimer mixture of L-isoleucine and D-alloisoleucine in a reaction medium to form a complex of D-alloisoleucine and the compound of formula I. The precipitated complex is decomposed by putting it in an alcohol to isolate D-alloisoleucine. In the latter process, L-isoleucine is suspended in an inert solvent which does not substantially dissolve amino acids, and epimerized in the presence of $C_1$–$C_5$ saturated lower fatty acid and salicylaldehyde.

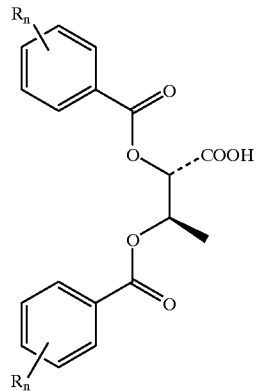

I

20 Claims, No Drawings

PROCESS FOR PREPARING D-ALLOISOLEUCINE AND INTERMEDIATES FOR PREPARATION

BACKGROUND OF THE INVENTION

The present invention concerns improvement in a process for preparing D-alloisoleucine, which is useful for preparing medicines, particularly, drugs for cardiovascular disease (typically, WO94/28,901), and a novel complex which occurs as the intermediate in the process of preparation thereof. The invention also concerns an improved process for epimerizing L-isoleucine for the purpose of producing D-alloisoleucine from L-isoleucine.

The present invention makes it possible to produce D-alloisoleucine, which has not been available in a large quantity, from L-isoleucine which is commercially mass-produced, by a simple process at a high yield.

In this specification RS-indication is used in relation to the configuration of tartaric acid and derivatives thereof. This is because the conventional DL(or dl)-indication may cause confusion, in fact, in the past there was a case where one researcher regarded an isomer as D-form while another indicated the same compound as L-form. As far as amino acids are concerned there is no such problem and thus conventional DL-indication is used. The term "isomerization" is used to encompass both racemization and epimerization. In some cases these are represented by the term "racemization".

PRIOR ART

D-alloisoleucine, or (2R,3S)-2-amino-3-methylpentanoic acid of formula II below

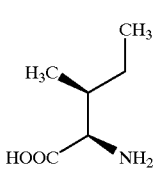

II is a stereoisomer of L-isoleucine which is one of essential amino acids. To date, it has been difficult to obtain D-alloisoleucine in a large quantity, because there has been established so far no process for preparation which can be carried out in an industrial scale.

Of the known processes for preparing this compound the following two are important. One is resolution of racemate of alloisoleucine, and the other is to separate D-allo form from mixture of epimers obtainable by epimerizing L-isoleucine of formula III below:

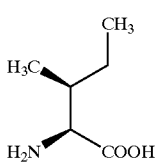

III

[See, for example, T. Kaneko ed. "Amino Acid Industry, Synthesis and Utilization", Kodansha Scientific, 1973, p.133].

The above mentioned optical resolution of racemic alloisoleucine can be carried out by resolving N-acetyl derivative thereof using quinine as the resolving agent [W. A. Huffmann, A. W. Ingersoll, J. Am. Chem. Soc., 73, 3366 (1951)]. This process is, however, not practical, because, in addition to the fact that it requires transformation of alloisoleucine to an N-acetyl derivative thereof, the racemate itself is not easily available.

On the other hand, epimerization of commercially produced L-isoleucine can be relatively easily practiced.[By, for example, U.S. Pat. No. 4,401,820 to Chibata et al.]

However, in all the known processes for resolution of epimer mixture, the epimers are resolved after being derived to derivatives, and it has been established no process which resolves the epimer mixture as it is. Reported processes are: recrystalization of N-formyl derivative from MEK [Dow Chemical, British Patent 704983 (1954)]; Cbz-protection or Boc-protection of the epimer mixture followed by separation relying on the difference in solubilities of optically active α-phenylethyl-amine salts [G. Flouret, S. H. Nagasawa, J. Org. Chem., 40, 2635 (1975)]; removal of L-isoleucine resulted from N-acetyl derivative by asymmetric hydrolysis using an enzyme and recovery of the remaining N-acetyl-D-isoleucine [P. Lloyd-Williams et al., J. Chem., Soc., Perkin Trans. I, vol. 1994, 1969]. Anyway in these processes, the resolved products are given as the derivatives, and therefore, further steps such as removal of substituents are necessary until the desired optically active compounds are recovered. These processes are troublesome and cannot be said to be practical.

Generally speaking, extensive research has been done on the resolution of amino acids. Most amino acids are usually resolved in the form of N-acyl derivatives or esters, and successful reports of resolution of non-derivatized amino acids are relatively few. Strong acidic resolving agents such as sulfonic acids, tartaric acid or mandelic acid are useful to resolve some non-dervatized amino acids, for example phenylglycine, phenylalanine, while no successful resolution of neutral aliphatic amino acids such as leucine and isoleucine is reported.

There has been known some cases where neutral amino acids, or amino acids having no functional group other than amino and carboxylic groups are derived to esters thereof, and the esters are resolved with dibenzoyl tartaric acid or its substituted derivative as the resolving agent. For example, benzyl ester of alanine is resolved by using (2R,3R)-dibenzoyl-tartaric acid, and in the process the salt of D-alanine ester with the tartaric acid derivative precipitates as the less soluble salt [W. Langenbeck, O. Herbst, Chem. Ber., 86, 1524 (1953)]. In case of ethyl ester of leucine, analogous to this, a salt of L-ester and (2R,3R)-dibenzoyl tartaric acid precipitates [W. Langenbeck, G. Zimmermann, Chem. Ber., 84, 524 (1951); G. Losse, H. Jeschkeit, Chem. Ber., 90, 1275, (1957)]. As examples of resolution of amino acids having no protecting group by using dibenzoyl tartaric acid as the resolving agent, only the resolution of lysine [F. J. Kearley, A. W. Ingersoll, J. Am. Chem. Soc., 73, 5783 (1951)] and resolution of asparagine [E. Fogassy, M. Acs, J. Gressay, Periodica Polytechnica, 20, 179 (1976)] are reported. No trial has been made, however, on direct optical resolution of neutral aliphatic amino acids such as alanine, valine, leucine, isoleucine without deriving them to esters and using dibenzoyl tartaric acid or substituted derivative thereof.

In production of optically active amino acids from racemates thereof it is desirable to recover the unnecessary enantiomer separated from the desired enantiomer and to subject to racemization or epimerization for recycling it to the optical resolution step and reusing. Particularly, for industrial practice of optical resolution this kind of isomerization is almost essential.

For the purpose of isomerization various methods have been proposed and practiced from the old days. The methods are summarized in regard to amino acids as follows [I. Chibata et al., "Kagaku Sosetsu" No. 4. Chemistry of Asymmetric Reactions, p.233–262, 1974]:
1) chemical methods,
2) thermal methods,
3) catalytic methods, and
4) enzymatic or biotechnological methods.

Of these methods usually those of 3, catalytic methods are the most suitable. A concrete example (above mentioned U.S. Pat. No. 4,401,820) comprises dissolving various amino acids in glacial acetic acid, adding salicylaldehyde to the solution in a molar ratio of 0.2 based on the amino acid, and heating to 100° C. for 1 hour. Then, racemization, the extent of which is as low as 3–35% if no aldehyde is added, proceeds to such a high level as 90–100%.

After racemization in this way, it is not necessarily easy to recover the target amino acids from the reaction mixture. In case where the amino acids are readily soluble in acetic acid it is necessary to concentrate the reaction solution under reduced pressure nearly to dryness, to dissolve the dried substance in a solvent such as alcohol or acetone, and to crystallize out the amino acids from the solution. In the cases of some specific amino acids, for example, phenylglycine, p-hydroxy-phenylglycine and serine, racemates of the amino acids crystallize out by simple cooling of the reaction solution using acetic acid as the reaction medium and the crystal can be separated by filtration. However, this procedure can be applied only to a limited number of amino acids. The higher the solubility of the Amino acid in acetic acid is, the larger the quantity of acetic acid to remove by concentration is. Due to the facts that energy consumption increases to an unbearable extent and that recovery of the aldehyde added as the catalyst is difficult, racemization of amino acids in acetic acid solvent is in many cases not suitable for industrial practice.

SUMMARY OF THE INVENTION

An object of the present invention is to provide a process for preparing D-alloisoleucine by direct optical resolution of epimer mixture of L-isoleucine and D-alloisoleucine without deriving them to derivatives, and therefore, through simple steps, at a high yield and a high purity. The intermediate, a complex of the resolving agent and D-alloisoleucine which occurs during the preparation of D-alloisoleucine constitutes a part of the invention.

Another object of the present invention is to solve the above noted problem residing in isomerization of amino acids and to provide an improved process for isomerization of amino acids, particularly, epimerization of isoleucine, which can be carried out at a low energy consumption and a high efficiency, and also facilitates recovery and reuse of the aldehydes used as the catalyst The latter process is useful for producing the epimer mixture which is used as the material for the former process. Thus, the object of the present invention includes provision of a consistent process for producing D-alloisoleucine, which is expensive and difficult to obtain in a large quantity, from L-isoleucine, which is less expensive and easily available in a large quantity.

DETAILED EXPLANATION OF THE PREFERRED EMBODIMENTS

The process for preparing D-alloisoleucine according to the present invention comprises the steps of combining a (2S,3S)-tartaric acid derivative of formula I:

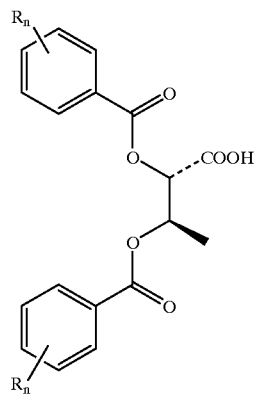

[in formula I, R stands for a hydrogen atom, a $C_1$–$C_3$ lower alkyl group, lower alkoxy group, chlorine atom, bromine atom and nitro group; and "n" is a number of 0, 1 and 2.] with an epimer mixture of L-isoleucine and D-alloisoleucine in a reaction medium, separating the precipitated complex of D-alloisoleucine and the compound of formula I, and isolating D-alloisoleucine by decomposing the separated solid complex.

The complex of the compound of formula I with L-isoleucine has a much higher solubility than that of the complex with D-alloisoleucine, and therefore, it is possible to obtain the complex with D-alloisoleucine of high optical purity by solid-liquid separation at a high yield which can be said almost quantitative.

It is possible to separate the resolving agent, tartaric acid-O,O'-diaroyl ester, by putting the complex of the compound of formula I with D-alloisoleucine in a lower alcohol such as methanol and ethanol. By this operation D-alloisoleucine of a high purity crystallizes out and can be further purified by a simple purification process.

Examples of the compound of formula I, (2S,3S)-tartaric acid-O,O'-diaroyl ester, are dibenzoyl-tartaric acid, di(p-toluoyl)-tartaric acid, di(3,4-dimethylbenzoyl)-tartaric acid, di(2-chlorobenzoyl) tartaric acid and so on. These compounds can be easily synthesized according to known methods, for example, by heating (2S,3S)-tartaric acid with a halide or anhydride of benzoic acid or substituted benzoic acid corresponding to the moiety of the compound to be prepared, and by hydrolyzing the resulting diaroyl-tartaric acid anhydride [C. L. Butler, L. H. Cretcher, J. Am. Chem. Soc., 55, 2605 (1933); Toray, Japanese Patent Disclosure No.07-138206]. Of these tartaric acid derivatives particularly useful are the following two which are easily available in commerce:

| Form | Abbreviation |
| --- | --- |
| Dibenzoyl (R = H) | "DBTA" |
| p-Toluoyl (R = p-Me, n = 1) | "DTTA" |

The amount of the tartaric acid derivative used as the resolving agent for the epimer mixture is chosen in the range of molar ratio 0.1 to 0.7. This is because, as described later, D-alloisoleucine constitutes 1:1-complex with (2S, 3S)-tartaric acid-O,O'-diaroyl esters. If the molar ratio of the tartaric acid derivative to the epimer mixture is low, the amount of the complex to crystallize out decreases, and thus yield will be low. On the other hand, at a molar ratio exceeding 0.6 complex of the tartaric acid derivative with L-isoleucine tends to crystallize out, and as the result, optical purity of the obtained D-alloisoleucine will be lowered. Thus, range of the amount of use of the resolving agent is, in the molar ratio to the epimer mixture, preferably, 0.3 to 0.5, more preferably, 0.4 to 0.5. Optical purity of D-alloisoleucine in the complex crystallizing out under this condition will be 90% de or higher, and sometimes gets to 97–98% de.

For crystallization of the complex, addition of achiral acid to the system in addition to the tartaric acid derivative as the resolving agent, gives better results. An achiral acid of a molar ratio to the epimer mixture 0.05–0.7, preferably, 0.4–0.6, improves optical purity of the complex of D-alloisoleucine and the tartaric acid derivative to crystallize out, and remarkably decreases the amount of the solvent to be used. As the achiral acid, an inorganic acids such as hydrochloric acid, sulfuric acid and phosphoric acid, and an organic acids such as formic acid, acetic acid and propionic acid can be used. An inorganic acid, particularly, hydrochloric acid is preferable.

In the optical resolution where an optically active acid or amine is used as the resolving agent to form a diastereomeric salt, it has been widely practiced to use the resolving agent of not an equivalent amount but a lower amount than the equivalent together with an achiral acid or a base in the amount to compensate the deficient amount and neutralize the system. This is called "Pope and Peachey Method" [J. Chem. Soc., 75, 1066 (1899)]. The above described embodiment of the present invention may be apparently understood as an example of Pope and Peachey Method. However, the embodiment should not be regarded in the same light with the known method, in view of the fact that one mole of the amino acid epimer and one mole of the tartaric acid derivative, which is a dibasic acid, constitutes the less soluble complex, which itself is acidic and not neutralized, and that excess acid is further added thereto.

As the medium for forming the complex, water, lower alcohols and mixtures thereof can be conveniently used. Examples of the lower alcohols are methanol, ethanol, 1- and 2-propanols. Water only can be used and give good results as far as the yield of the complex and optical purity of D-alloisoleucine is concerned. However, relatively large quantity of water is required. From this point of view a mixed solvent prepared by adding a certain amount of methanol to water is advantageously used, because the amount of the medium can be so reduced as ⅔ to ½ and thus, the operation will be more efficient. The complex formation using the water-methanol mixed solvent is also advantageous due to the fact that the crystal thus formed is easy to filter. Suitable amount of methanol will be 10 to 30 wt. % in the mixed solvent. Methanol of so low percentage as less than 10% will not give the benefit of reduced amount of the solvent, while a higher percentage exceeding 30% results in decreased yield of the complex.

Provision of the system, i.e., incorporation of the epimer mixture, the tartaric acid derivative and the solvent, inclusive of addition of the achiral acid, if used any, can be done in any sequence. It should be noted, however, that the tartaric acid derivatives, the resolving agent, exhibit lower solubilities in water and that they are readily hydrolyzed under strong acidic conditions. Therefore, the following sequence of steps is recommended: the epimer mixture is first put in the solvent with a part of the achiral acid, if added any, to dissolve the epimer mixture, then, the resolving agent is added directly, or preferably, in the form of lower alcohol solution. After this the rest of the achiral acid is added to adjust the system to the targeted composition. It is not necessary to form a homogeneous solution. The intended steps can be carried out in a non-homogeneous system where the reactants are partly dissolved and partly dispersed.

The system (a solution or a dispersion) must be thoroughly stirred. Heating under stirring is preferable from the view to stabilize production of the complex of high quality. After being heated the system is slowly cooled to room temperature or lower so that the complex may sufficiently crystallize out. The precipitated crystal is then separated by filtration or centrifugation.

The obtained complex, as understood from the data of elemental analysis and $^1$H-NMR spectrum, which are shown in the working examples described later, contains the amino acid and the resolving agent in a molar ratio of 1:1. Based on the water content analysis (Karl-Fischer method) it was found that, depending on the resolving agent, 1 to 2 molecules of water may be included in the complex. In other words, in case where DBTA, which has no substituent, is used, a non-hydrated complex is obtained, while in case where DTTA, which is substituted with a methyl group, is used, a hydrated complex containing 1–2 water molecules is given.

The type of the bonds between D-alloisoleucine and the tartaric acid derivative in the complex is considered to be, on the basis of the fact that it readily decomposes in an alcohol, weaker than those in ordinary diastereomeric salts. Fogassy et al. investigated the diastereomers formed between alicyclic amines and DBTA, and proposed to judge whether it is a typical ionic salt or a looser molecular complex combined with hydrogen bonds by IR absorption spectrum [Tetrahedron, 52(5), 1637–42 (1996)]. According to them, in case where an ionic bond exists, an absorption by ionized amino group appears at 3400–80 $cm^{-1}$, and absorptions by carboxylic group at 1610–30 $cm^{-1}$ and 1320–80 $cm^{-1}$, while in case where no ionic bond exists an absorption by amino group appears at around 3400 $cm^{-1}$ and a strong absorption by carboxylic group, around 1720 $cm^{-1}$.

The complex obtained in the present invention is not a complex with alicyclic amines which Fogassy et al studied but a complex with amino acids. The amino acids themselves have carboxylic groups, and due to possibility of forming intramolecular salts, it is difficult to discriminate the type of bonding in the complex on the basis of IR absorption spectrum. The complex of the present invention contains three carboxylic group per one amino group, and therefore, from the ionic point of view it is entirely unneutralized compound. On the basis of this fact and the above mentioned tendency to easily decompose in an alcohol, it is likely that this complex is not a salt formed by ionic bonds but a complex combined by weak bonds such as hydrogen bonds.

In the mother liquor from which the complex was recovered L-isoleucine remains in the dissolved state. This can be recovered and epimerized by the process described above for reuse. More specifically, after distilling out the solvent alcohol by heating the liquor, the residue is subjected to acidification and extraction with a suitable organic solvent for separation of less soluble resolving agent, or the tartaric acid derivative. Neutralization of the remaining aqueous solution to the isoelectric point results in crystallization of isoleucine.

The procedures to obtain the desired optically active D-alloisoleucine from the complex crystal separated as described above may comprise, if the conventional way is followed, putting the complex in an acidic aqueous solution to dissolve the amino acid, removing less soluble tartaric acid derivative by extraction with a water-inmiscible organic solvent, neutralizing the acidic aqueous solution of the amino acid to bring the pH thereof to the isoelectric point, and recovering crystallized D-alloisoleucine by solid-liquid separation. Separation of the amino acid following to the solvent extraction of the resolving agent can be done also by ion exchange.

The complex of the present invention is, as described above, a substance which so easily decomposes as it has convenient property that, by simple operation of putting it in a highly polar solvent such as methanol, ethanol and isopropanol, the tartaric acid derivative, the resolving agent, dissolves in the solvent and D-alloisoleucine crystallizes itself to be separated. In order to ensure the separation it is effective to add a base such as triethylamine, which dissolves well in alcohols, in an amount of 1–2 equivalent based on the amino acid. A more effective way is to use a solvent prepared by adding 2–20% of water to alcohol. It was found that, when isopropanol containing about 10% of water is used, D-alloisoleucine of a high optical purity containing substantially no tartaric acid derivative, the resolving agent, can be obtained with such a high rate of recovery as 90% or more based on the complex. The optical purity of the amino acid thus obtained is higher than that of the amino acid in the complexe, and therefore, the procedures of decomposition and crystallization themselves have purifying effect.

The solvent in which the complex is decomposed may be, in addition to the above mentioned lower alcohols, various highly polar solvents such as esters, for example, methyl acetate and ethyl acetate, and ketones, for example, acetone and methylethyl ketone. In any case, it is preferable to use the solvents with addition of water of 5–10%.

The mother liquor from which the amino acid crystallized out by decomposition of the complex was separated contains the tartaric acid derivative, the resolving agent, with a small amount of the amino acid. Concentration of this mother liquor by evaporation of the solvent gives the resolving agent in the form of solid. The recovered resolving agent may be reused, as it is or after being purified, if necessary, for the subsequent batch of the complex formation.

The epimer mixture used as the starting material of preparation of D-alloisoleucine according to the present invention can be obtained by isomerizing commercially available L-isoleucine by a conventional process. Isoleucine has two asymmetric carbon atoms at 2-position at which an amino group is attached and 3-position at which a methyl group is attached. The latter, the carbon atom of the 3-position, does not be isomerized under ordinary conditions and only the carbon atom at 2-position is isomerized to form an epimer mixture of L-isoleucine and D-alloisoleucine. For this isomerization or epimerization any conventional method for racemizing optically active amino acids may be used. Specifically, the method comprises mixing the amino acid with an acid or base catalyst and heating, heating at neutral phase under applying pressure, when necessary, and so on.

Isomerization of isoleucine proceeds at a relatively slow rate. It is practical to heat it in the presence of an aldehyde such as salicylaldehyde to isomerize by way of a Schiff base. Such isomerization or epimerization is already reported (above noted U.S. Pat. No. 4,401,820). According to the patent heating isoleucine in glacial acetic acid in the presence of catalytic amount of salicylaldehyde to 100° C. for 1 hour causes epimerization to the extent of 93%.(If aldehyde is absent, rate of epimerization under the same reaction condition reaches only 4%.)

A drawback residing in this method is difficulty in separating the epimer mixture from the reaction mixture after epimerization. As a solution of this problem, the inventors adopted use of an aromatic hydrocarbon or an inert solvent which has relatively low solubility to water as the reaction medium for the epimerization. Use of this kind of solvent and filtering off of the amino acid mixture crystallized out by cooling after the reaction makes it possible to obtain the epimer mixture of a high purity only by washing the filter cake with a solvent.

The process for isomerization according to the present invention can be applied not only to the epimerization of isoleucine but also generally to isomerization of optically active amino acids. The following explanation refers, therefore, generally to the amino acids.

The aromatic hydrocarbons which are used in the invention as the important reaction media for the isomerization of the amino acids dissolve little quantity of amino acids. Apparently, therefore, the reaction proceeds in the state where the optically active amino acid is dispersed in the medium. The racemate or the epimer mixture formed by the isomerization is also not soluble in the reaction medium and precipitates out. This precipitation can easily be separated by filtration. In view of the fact that, as seen from the working examples described below, the finer the material optically active amino acid particles are, the better the results obtained are both in the rate of racemization and the rate of recovery of the amino acid, it is speculated that the lower fatty acid added in a small amount to the reaction medium assists sequential and partial dissolution of the optically active amino acid, and that the isomerization reaction itself proceeds in a homogeneous system.

Anyway, however, the fact that the isomerization reaction of optically active amino acids proceeds in the state of dispersion or suspension and the reaction products is obtained at a high purity is contrary to the common understanding that this kind of reaction goes well in the state of solution. The present invention is grounded on this surprising discovery.

The optically active amino acids isomerizable in accordance with the present invention encompasses natural and synthetic α-amino acids over a wide range. Particularly, isomerization of neutral amino acids, specifically, alanine, α-aminobutanoic acid, valine, leucine, isoleucine, serine, threonine, cystine, cysteine, methionine, tryptophan, phenylalanine, tyrosine, DOPA, phenylglycine, p-hydroxyphenyl glycine completes in a practical reaction period of time, and after the reaction crystal of the isomerized amino acids precipitates just by cooling and the product can be obtained at a high yield only by filtration. The case where the present invention is the most significantly applied is, as noted above, the reaction to isomerize optically active isoleucine to form the epimer mixture of L-isoleucine and D-alloisoleucine.

The material optically active amino acids may of course be not only pure substances containing little optical isomers but also of low optical purity, or a mixture of racemate and one of the optical isomers. Needless to say, the present process can be applied to mixtures of two or more amino acids.

There are many inert solvents which do not substantially dissolve the amino acids and can be used in the invention. They are aliphatic hydrocarbons such as hexane, heptane, octane, cyclohexane and methylcyclohexane, aromatic hydrocarbons such as benzene, toluene, xylene and halogenated benzenes, ketones such as acetone, methylethyl ketone and methylisobutyl ketone, esters such as ethyl acetate, isopropyl acetate and butyl acetate, ethers such as diethyl ether, tetrahydrofurane, 1,4-dioxane and methyl-t-butyl ether, halogenated hydrocarbons such as methylene chloride, chloroform, carbon tetrachloride and 1,2-dichloroethane, and alcohols such as isopropanol, n-butanol and isobutanol.

Of these solvents aromatic hydrocarbons are preferable. Particularly, toluene or xylene enables quick isomerization and higher recovery of racemates, and therefore, advantageously used. These solvents are less expensive, readily available and recovery thereof is easy.

The lower fatty acids suitable to be added to the reaction medium are $C_1$–$C_5$ saturated fatty acids, more specifically, formic acid, acetic acid, propionic acid, butanoic acid and pentanoic acid. It is advantageous to use acetic acid and propionic acid because they are easily available and effectively accelerate the isomerization reaction. Suitable amount of use of the fatty acid is in the range of 3–10 moles per mole of the amino acid. At a too small amount of the fatty acid used reaction rate of the isomerization is low. At a larger amount the rate of reaction will be improved, while the rate of recovery of the product decreases, because the amino acids dissolve in the fatty acid. Anyway, however, the main medium of the reaction is the inert solvent, and thus the amount of the fatty acid used is much smaller than the cases where the fatty acid is used as the reaction medium in the known process.

The aldehydes used as the catalyst may be any of aliphatic and aromatic aldehydes as far as they exhibit catalytic effect on the isomerization of amino acids. Examples of the aliphatic aldehydes are formaldehyde, acetaldehyde, propionaldehyde and butyraldehyde, and those of the aromatic aldehydes are benzaldehyde and salicylaldehyde. In addition to these, heterocyclic aldehyde such as furfural can be used. In this specification the term "aromatic aldehyde" is intended to include the heterocyclic aldehyde. Benzaldehyde and salicylaldehyde may be substituted with a halogen atom or atoms. Particularly good results are given by salicylaldehyde. Suitable amount of use of salicylaldehyde is 0.01–0.3 mole, preferably, 0.05–0.2 mole per 1 mole of the amino acid used.

The process for isomerization according-to the present invention is carried out by heating the system which consists of a solvent, an optically active amino acid, a lower fatty acid and an aldehyde composed by any sequence of addition, to 60–120° C., preferably, 80–110° C. under stirring. The reaction temperature is conveniently the reflux temperature of the solvent. Rate of reaction depends on the solvent, the material amino acid and the reaction conditions. Usually, the reaction almost completes in 1–10 hours. Because the reaction proceeds, as described above, under the condition of incomplete dissolution of the amino acid, it is essential, for the purpose of realizing high reaction rate and conversion, to use the material amino acid in the form of particles as fine as possible, and to ensure effective stirring.

After completion of the isomerization the reaction solution is cooled to a temperature around the room temperature, the precipitated crystal of the amino acid is separated by filtration and rinsed with an appropriate solvent, and thus, isomerized product of the amino acid is obtained at a high purity. The mother liquor of filtration contains major parts of the lower fatty acid and the aldehyde and can be reused as it is for the subsequent isomerization step with replenishment of the losses.

A variety of merits is offered by the present invention as follows. At first, contrary to the conventional process for preparing D-alloisoleucine which requires troublesome steps of transforming racemate or the epimer mixture of L-isoleucine and D-alloisoleucine to N-acyl derivatives, and optical resolution using a known resolving agent followed by hydrolysis, or asymmetric hydrolysis using an enzyme, the present process starts from L-isoleucine and comprises relatively simple steps of epimerization and complex formation of the epimer mixture with a tartaric acid derivative followed by decomposition of the complex, thus enables commercial production of D-alloisoleucine of a high optical purity at a high yield.

In the optical resolution of amino acids, the cases where the amino acid can be directly resolved with a resolving agent without protection of amino groups or carboxylic groups are quite limited. As to the direct resolution using a tartaric acid derivative such as DBTA and DTTA the cases reported to date are only two which relate to asparagine and lysine. As to direct resolution of neutral aliphatic amino acid such as alanine, valine and leucine possibility of success has not been discussed in regard to not only the tartaric acid derivatives but also to the other resolving agent. The present invention which enables direct resolution of the epimer mixture of L-isoleucine and d-alloisoleucine under the circumstances is epoch-making.

L-isoleucine is produced in large quantity and therefore, it is easy to obtain at a low price. The (2S,3S)-tartaric acid-O,O'-diaroyl esters are also easily available. The amount of use is such a small amount as molar ratio of around 0.5 based on the epimer mixture, and the resolving agent can be recovered at a high rate and reused.

In a preferred embodiment addition of a small amount of an inorganic or an organic acid, particularly, an inorganic acid together with the resolving agent makes it possible to remarkably reduce the necessary amount of the medium which brings about significant improvement in the productivity.

Decomposition of the complex can be readily carried out only by putting the complex in a lower alcohol, preferably, a lower alcohol mixed with a small amount of water, and the targeted D-alloisoleucine can be separated at a high yield.

L-isoleucine remaining after separation of D-alloisoleucine from the epimer mixture can be epimerized again by the process for isomerizing optically active amino acids according to the present invention and reused as the material for producing D-alloisoleucine. This results in efficient utilization of the material.

The novel process for isomerizing amino acids according to the present invention comprises the steps, which have not been tried, of suspending the amino acid in a medium of an inert solvent which dissolves substantially no amino acid and to which a lower fatty acid is added, isomerizing the amino acid by the catalytic effect of an aldehyde, filtering the isomerized amino acid and rinsing. The steps are quite simple, and enjoys remarkably decreased energy consumption, because the step of evaporating acetic acid solution, which is essential in the known process, is no longer necessary in the invention. The running cost of the process is low because of the facts that the mother liquor of filtration can be reused for the subsequent batch as it is, and that loss of relatively expensive aldehyde is not significant. Thus, the process is advantageous from the view points of high utilization of resources and ecological protection, and useful for commercial production of various optically active amino acids.

To summarize the invention, it provides the first process which enables industrial production of D-alloisoleucine, well known but very difficult to obtain in quantities to date, and opens vast possibility of utilizing this compound as new component or starting material for various biologically active substances useful as pharmaceuticals and agrochemicals.

EXAMPLES

A. Production of D-Alloisoleucine from Epimer Mixture of L-Isoleucine and D-Alloisoleucine Measurement of optical purities of the epimer mixture and D-alloisoleucine in the following examples was done with HPLC under the following conditions.

Column: Daicel CHIRALPAK MA(+) φ0.46 cm×5 cm
Mobile Phase: 2 mmol $CuSO_4$+MeOH (85:15)
Flow Rate: 0.5 mL/min.
Column Temperature: 30° C.
Detector: Nihon Bunko UV-975, Wave Length 254 nm

Example A-1

5 g (38.1 mmol) of an epimer mixture of L-isoleucine and D-alloisoleucine was suspended in 90 mL of water in an reaction vessel. To the suspension 6.83 g (19.1 mmol) of (2S,3S)-DBTA was added, and the mixture was heated to 70° C. and maintained at this temperature for 1 hour under stirring. Slurry formed by reaction of the amino acids and the DBTA was allowed to stand still to cool, and subjected to solid-liquid separation at 25° C. The solid obtained was rinsed twice with 10 mL each of water. 7.77 g of a 1:1-complex of D-alloisoleucine and (2S,3S)-DBTA was obtained as white crystal. Yield (based on the epimer mixture) as 41.7%, and the optical purity, 95.6% de.

The analysis of the resulting complex is shown below:
Melting point: 175.5–176.5° C.

IR KBr pellet ($cm^{-1}$): 3156, 2972, 2942, 2882, 1733(s), 1692(s), 1601(m), 1528(m), 1320, 1266(s), 1118(s), 719(s)

$^1$H-NMR (270 MHz, MeOH-$d_4$) δ (ppm): 0.97 (t, 3H, J=4.0 Hz); 1.00 (t, 3H, J=4.0 Hz); 1.24–1.40 (m, 1H); 1.43–1.59 (m, 1H); 2.01–2.14 (m, 1H); 3.71 (d, 1H, J=3.5 Hz); 4.90 (s, 7.5H); 5.94 (s, 2H); 7.50 (t, 4H); 7.64 (m, 2H); 8.11 (m, 4H).

Elemental Analysis Observed: C 59.0%, H 5.6%, N 3.1% Calculated($C_{24}H_{27}NO_{10}$): C 58.9%, H 5.6%, N 2.9%

Water Content (Karl-Fischer method): 0.53% (monohydrate, calculated value 3.55%)

A mixture of 27 mL of 2-propanol and 3 mL of water was prepared, and 3 g of the above complex was put in the mixture.

The mixture was heated to reflux for 1 hour, and then cooled. After solid-liquid separation at 25° C. the solid matter was rinsed three times with 4 mL each of 2-propanol. D-alloisoleucine, 0.71 g, was obtained as white crystal. The yield was 88.3% (based on the complex), and the optical purity (HPLC), 100% de.

Example A-2

5 g (38.1 mmol) of the epimer mixture the same as used in Example A-1 was suspended in 49 ML of water in a reaction vessel, to which 1.98 g (19.1 mmol) of 35%-hydrochloric acid was added. Then, analogous to Example 1, 6.83 g (19.1 mmol) of (2S,3S)-DBTA was added to the suspension, and the mixture was heated to 70° C. and maintained at this temperature for 1 hour under stirring. The same treatment as in Example 1 gave 8.21 g of 1:1-complex of D-alloisoleucine with (2S,3S)-DBTA in the form of white crystal. The yield (based on the epimer mixture) was 44.0%, and the optical purity, 96.2% de.

8.0 g of this complex was put in a mixture of 72 mL of 2-propanol and 8 mL of water to decompose the complex as done in Example 1. D-alloisoleucine thus obtained weighed 1.90 g. The yield (based on the complex) was 88.4%, and the optical purity (HPLC), 100% de.

Example A-3

5 g (38.1 mmol) of the epimer mixture the same as used in Example 1 was suspended in 75 ml of water in a reaction vessel. A solution of 6.83 g (19.1 mmol) of (2S,3S)-DBTA in 10 mL of methanol was added dropwise to the mixture, and the mixture was heated to 70° C. and maintained at this temperature for 1 hour under stirring. The same procedures as in Example 1 gave 7.39 g of a complex. The yield (based on the epimer mixture) was 39.6%, and the optical purity, 95.6% de.

Example A-4

5 g (38.1 mmol) of the epimer mixture the same as used in Example A-1 was added to 40 mL of water in a reaction vessel to suspend, to which, as done in Example 2, 1.98 g (19.1 mmol) of 35%-hydrochloric acid was added. Then, a solution of 6.83 g (19.1 mmol) of (2S,3S)-DBTA in 10 mL of methanol was added dropwise to the suspension, and the resulting mixture was heated to 70° C. and maintained at this temperature for 1 hour under stirring. After cooling by standing still the reaction mixture was further stirred at 25° C. for 1 hour, and the solid substance was separated from the liquid and rinsed with 10 mL of water. The obtained complex weighed 8.47 g. The yield (based on the epimer mixture) was 45.4%, and the optical purity, 95.4% de.

Example A-5

50 g (380 mmol) of the epimer mixture the same as used in Example A-1 was added to 360 mL of water in a reaction vessel, to which 8.0 g (77 mmol) of 35%-hydrochloric acid was added, and the mixture in the vessel was stirred to form a slurry. Then, a solution of 61.3 g (17.1 mmol) of (2S,3S)-DBTA in 100 mL of methanol and 80 mL of water was added dropwise to the slurry. Further 11.9 g (114 mmol) of 35%-hydrochloric acid diluted with 50 ml of water was added to the slurry, and the slurry was heated to 70° C. and maintained at this temperature for 1 hour under stirring. After being cooled spontaneously the reaction mixture was further stirred at 25° C. for 1 hour, and the solid substance was separated from the liquid. The solid was rinsed twice with each 100 mL of water, and then separated by filtration and dried. The obtained complex weighed 84.7 g. The yield (based on the epimer mixture) was 45.5%, and the optical purity, 94.8% de.

The mother liquor remaining after filtration and the washing were combined, and methanol was distilled off. The concentrated liquor was subjected to extraction with 200 mL of methyl-t-butyl ether to remove the resolving agent. The remaining solution was further concentrated and neutralized to isoelectric point (pH 5.94), and precipitated isoleucine was recovered.

80.0 g (163 mmol) of the complex obtained by the above procedures was put in a mixture of 720 mL of 2-propanol and 80 mL of water. The mixture was heated under reflux for 1 hour, and after cooling, solid substance was separated from the mixture at 25° C. The solid was rinsed three times with 80 mL each of 2-propanol and dried. Thus, 19.0 g of D-alloisoleucine was obtained as white crystal. Yield (based on the complex): 89.0%, Optical Purity: 99.9% de.

The above washing was combined with the filtrate solution, and the combined liquor was heated to distill off 2-propanol. 100 mL of methanol was added to the concentrated residue to form a solution, which contained about 58 g of (2S,3S)-DBTA together with a small amount of isoleucine, which could be used for the subsequent cycle of optical resolution.

Example A-6

5 g (38.1 mmol) of the epimer mixture the same as used in Example A-1 was added to 90 mL of water in a reaction vessel, and further, 7.36 g (19.0 mmol) of (2S,3S)-DTTA was added. The mixture was heated to 70° C., and maintained for 1 hour under stirring. Slurry resulting from the reaction was allowed to stand to cool, and subjected to solid-liquid separation at 25° C. The solid substance was rinsed twice with each 10 mL of water. The white crystal thus obtained weighed 9.2 g, which was considered to be a complex of D-alloisoleucine:(2S,3S)-DTTA: water in a ratio of 1:1:1–2 from the analytical data shown below. Yield (based on the epimer mixture) was 44.3%, and the optical purity, 94.8%.

Analytical data of this complex are shown below. The data indicate that the ratio of the amino acid and DTTA is 1:1. Though the analysis of water content and the elemental analysis are not in accordance, it is speculated that one mole or two moles of water are combined in the complex.

Melting point: 157–161° C.

IR KBr pellet (cm$^{-1}$): 3526, 2966, 2924, 1717(s), 1609(s), 1546(m), 1259(s), 1176, 1123, 1108(s), 755(s).

$^1$H-NMR (270 MHz, MeOH-d$_4$) δ (ppm): 0.97 (t, 3H, J=4.0 Hz); 1.00 (t, 3H, J=4.0 Hz); 1.26–1.40 (m, 1H); 1.43–1.58 (m, 1H); 2.03–2.13 (m, 1H); 2.42 (s, 6H); 3.70 (d, 1H, J=3.5 Hz); 4.89 (s, 11H); 5.91 (s, 2H); 7.31 (d, 4H); 8.03 (d, 4H).

Elemental Analysis Observed: C 58.9%, H 6.1%, N 2.8% Calculated (C$_{26}$H$_{31}$NO$_{10}$.H$_2$O): C 58.3%, H 6.2%, N 2.6% (C$_{26}$H$_{31}$NO$_{10}$.2H$_2$O): C 56.4%, H 6.4%, N 2.5%

Water Content (Karl-Fischer method): 6.47% (calculated as dihydrate: 6.51%)

8.0 g of the above complex was added to 80 mL of methanol and 1.6 g of triethylamine was added thereto, and the mixture was heated under reflux for 1 hour. The solid substance filtered after cooling the mixture was rinsed with 2 mL of methanol. White crystal, D-alloisoleucine, thus obtained weighed 1.48 g. The yield was 76.8% from the complex, and the optical purity, 99.4% de.

B. Preparation of Isoleucine Epimer Mixture and Amino Acid Racemates

In the following Examples degrees of racemization and epimerization of the amino acids were calculated on the basis of the optical purities measured with HPLC. Analysis of the amino acids was done under the conditions shown in Table 1.

TABLE 1

Analysis of Amino Acids

| Amino Acid | Column | Mobile Phase CUSO4 2 mM (%) | IPA (%) | MeOH (%) | Flow Rate (mL/min) | Column Temp.(° C.) |
|---|---|---|---|---|---|---|
| alanine | A | 100 | 0 | 0 | 0.5 | 30 |
| valine | A | 100 | 0 | 0 | 1.2 | 40 |
| leucine | A | 95 | 5 | 0 | 1.0 | 30 |
| isoleucine | A | 95 | 5 | 0 | 1.0 | 30 |
| phenylalanine | A | 90 | 10 | 0 | 1.0 | 30 |
| tryptophan | B | 85 | 0 | 15 | 0.8 | 40 |
| methionine | A | 95 | 5 | 0 | 1.0 | 30 |
| serine | A | 100 | 0 | 0 | 0.2 | 40 |

Column A: SUMICHIRAL OA-5000 OA-5000 5μm 100 4.6 mm × 15 cm
Column B: DAICEL CHIRALPAK MA(+) φ 4.6 mm × 5 cm
Detector: Nihon Bunko UV-975 Wave Length 254 nm The degree of isomerization (degree of racemization and degree of epimerization) is defined by the following equation:

$$\text{Degree of Isomerization}(\%) = \{(P_0 - P_1)/P_0\} \times 100$$

wherein $P_0$ stands for optical purity of the amino acid before the isomerization, and $P_1$, for that after the isomerization.

Example B-1

Various L-amino acids were subjected to racemization. The following procedures are given by taking isoleucine as the example. 5.0 g (38.12 mmol) of L-isoleucine was suspended in 25 mL of toluene. 8.7 mL (152.5 mmol) of acetic acid and 0.93 g (7.62 mmol) of salicylaldehyde were added to the mixture. The mixture was heated for 2 hour under reflux, and then, cooled to room temperature. Precipitated crystal was separated by filtration, rinsed three times with 5 mL each of toluene, and dried. 4.45 g of isoleucine (yield 89%) was obtained with degree of epimerization 89%. The results of the racemization of the various amino acids inclusive of isoleucine are shown in Table 2.

TABLE 2

| No. | Amino Acid | Degree of Racemization (%) | Yield (%) |
|---|---|---|---|
| 1 | alanine | 94 | 93 |
| 2 | valine | 48 | 90 |
| 3 | leucine | 98 | 88 |
| 4 | isoleucine* | 89 | 89 |
| 5 | phenylalanine | 85 | 90 |
| 6 | tryptophan | 82 | 87 |
| 7 | methionine | 86 | 86 |
| 8 | serine | 81 | 92 |
| 9 | aminobutanoic acid | 96 | 85 |

*Epimer mixture of L-isoleucine and D-alloisoleucine

Example B-2

Epimerization of L-isoleucine was carried out to determine the degree of epimerization. The epimerization procedures comprise suspending 5.0 g of L-isoleucine in 25 mL of toluene, with addition of acetic acid in molar ratio of 4 and salicyl-aldehyde in molar ratio of 0.2, and heating the mixture to reflux for 1, 2 or 3 hours under stirring. After the reaction periods the reaction mixtures were cooled to room temperature. The crystal thus precipitated was separated by filtration, rinsed three times with 5 mL each of toluene, and dried. The degree of epimerization and the yield of the recovered epimer are shown in

TABLE 3

| Reaction Period (hr) | Degree of Epimerization (%) | Yield (%) |
|---|---|---|
| 1 | 55 | 90 |
| 2 | 69 | 89 |
| 3 | 100 | 86 |

Example B-3

The influence of solvents on the isomerization of amino acids was investigated in regard to epimerization of L-isoleucine. 10.0 g of L-isoleucine was suspended in 50 mL of various solvents enumerated in Table 4, to which acetic acid in the molar ratio 4 and salicylaldehyde in the molar ratio 0.2 were added, and the mixture was heated to reflux for 6 hours under stirring. After the reaction the reaction mixtures were cooled, the precipitated crystals were separated by filtration, rinsed with 10 mL each of the solvent the same as that used in the reaction, and dried. The degree of epimerization and the yield of recovered epimer are shown in Table 4 together with the reaction temperatures, i.e., reflux temperatures of the solvents.

TABLE 4

| No. | Solvent | Degree of Epimerization (%) | Yield (%) | Reflux Temp. (° C.) |
|---|---|---|---|---|
| 1 | methylcyclohexane | 100 | 96 | 92 |
| 2 | benzene | 49 | 95 | 80 |
| 3 | methylethylketone | 98 | 94 | 89 |
| 4 | isopropyl acetate | 100 | 84 | 98 |
| 5 | 1,4-dioxane | 82 | 77 | 106 |
| 6 | 1,2-dichloroethane | 99 | 85 | 87 |
| 7 | isopropanol | 40 | 90 | 80 |

Example B-4

The influence of solvents on the isomerization of amino acids was further investigated with respect to racemization of L-amino acids in aromatic solvents (benzene, toluene and xylene). 5.0 g each of L-amino acids listed in Table 5 were suspended in 25 mL each of the three solvents, to which acetic acid in the molar ratio 4 and salicylaldehyde in the molar ratio 0.2 were added. The mixtures were heated to reflux for 2 hours under stirring. After the reaction the reaction mixtures were cooled to room temperature. The precipitated crystals were separated by filtration and rinsed with 5 mL each of the solvent the same as that used in the reactions. The degree of racemization and the yield are shown in Table 5.

TABLE 5

| No. | Amino Acid | Solvent | Degree of Isomerization (%) | Yield (%) |
|---|---|---|---|---|
| 1 | alanine | benzene | 31 | 94 |
| 2 | alanine | toluene | 94 | 93 |
| 3 | alanine | xylene | 98 | 89 |
| 4 | valine | benzene | 4 | 96 |
| 5 | valine | toluene | 48 | 90 |
| 6 | valine | xylene | 84 | 82 |
| 7 | leucine | benzene | 97 | 81 |
| 8 | leucine | toluene | 98 | 88 |
| 9 | leucine | xylene | 89 | 74 |
| 10 | isoleucine* | benzene | 14 | 77 |
| 11 | isoleucine* | toluene | 89 | 89 |
| 12 | isoleucine* | xylene | 98 | 76 |
| 13 | phenylalanine | benzene | 68 | 85 |
| 14 | phenylalanine | toluene | 85 | 90 |
| 15 | phenylalanine | xylene | 85 | 78 |
| 16 | serine | benzene | 55 | 96 |
| 17 | serine | toluene | 81 | 92 |
| 18 | serine | xylene | 89 | 93 |

Reflux Temp.: benzene 83° C. toluene 104° C. xylene 118° C.

Example B-5

Influence of the kind of aldehydes on the epimerization of isoleucine was investigated in regard to six aldehydes. 5.0 g of isoleucine was suspended in 25 mL of toluene, to which acetic acid in the molar ratio 4 and aldehydes listed in Table 6 (molar ratio 0.2) were added. The dispersions were heated to reflux for 2 hours under stirring. After the reaction the reaction mixtures were cooled to room temperature. Crystals thus precipitated were separated by filtration, rinsed three times with each 5 mL of toluene, and dried. The degrees of epimerization and the yields are shown in Table 6 together with the kind of aldehydes used

TABLE 6

| No. | Aldehyde | Degree of Epimerization (%) | Yield (%) |
|---|---|---|---|
| 1 | salicylaldehyde | 89 | 90 |
| 2 | 5-chlorosalicylaldehyde | 46 | 87 |
| 3 | 3,5-dichlorosalicylaldehyde | 17 | 80 |
| 4 | benzaldehyde | 93 | 78% |
| 5 | furfural | 45 | 59 |
| 6 | butyraldehyde | 73 | 91 |

Example B-6

To determine the optimun conditions for industrial practice of epimerization of L-isoleucine trials were carried out under different epimerization conditions in the case where toluene is chosen as the solvent, acetic acid as the fatty acid and salicylaldehyde as the aldehyde. Molar ratios of the starting material to the solvent, scale of practicing, molar ratios of acetic acid and salicylaldehyde to the amino acid, and the reaction periods were varied. The reaction temperature was constant at the boiling point of toluene under normal pressure, 104° C. The degrees of epimerization and the yields are shown in Table 7.

TABLE 7

| No. | L-iso-leucine (g) | Toluene (mL) | Acetic Acid (molar ratio) | Salicyl Aldehyde (molar ratio) | Reaction Period (hr) | Degree of Epimerization (%) | Yield (%) |
|---|---|---|---|---|---|---|---|
| 1 | 5 | 25 | 4 | 0.2 | 2 | 89 | 89 |
| 2 | 5 | 25 | 4 | 0.2 | 3 | 100 | 86 |
| 3 | 5 | 50 | 10 | 0.2 | 3 | 95 | 79 |
| 4 | 10 | 40 | 3 | 0.1 | 6 | 100 | 83 |
| 5 | 10 | 40 | 4 | 0.1 | 5 | 97 | 81 |
| 6 | 10 | 40 | 3 | 0.2 | 4 | 100 | 82 |
| 7 | 50 | 200 | 5 | 0.2 | 2 | 95 | 91 |
| 8 | 120 | 600 | 4 | 0.2 | 3 | 100 | 90 |

Example B-7

In the mother liquor (typically, toluene solution) used for epimerization of L-isoleucine from which the epimers were recovered by filtration contains carboxylic acid and aldehyde (typically, acetic acid and salicylaldehyde). In order to practice industrial epimerization advantageously it is necessary to recover and reuse the mother liquor. For the purpose of ascertaining this trial for the repeated use of the mother liquor was carried out. The procedures of this trial were to determine the amounts of acetic acid and salicylaldehyde contained in the mother liquor of the first batch of the epimerization, and then to replenish the consumed amounts for the second batch. This was repeated six times. The reaction conditions were: L-isoleucine 10.0 g, toluene 50 mL, molar ratio of acetic acid to the amino acid 4, molar ratio of salicylaldehyde to the amino acid 0.2, and the reflux period 6 hours. The results of analysis and the amounts of replenishment at every batch are shown in Table 8 together with the yield of recovered epimer.

TABLE 8

| | | | Recovered Mother Liquor | | | | |
|---|---|---|---|---|---|---|---|
| | | | | Tol + | Supplement | | |
| Batch | L-Ile (g) | AcOH (g) | SA (g) | Ile (g) | AcOH (g) | SA (g) | Tol (g) | Yield (%) |
| 1 | 10.0 | — | — | — | 18.38 | 2.02 | 43.51 | 84 |
| 2 | 10.0 | 14.87 | 1.37 | 38.41 | 3.43 | 0.50 | 5.23 | 90 |
| 3 | 10.1 | 18.76 | 1.54 | 35.33 | 0 | 1.57 | 8.27 | 86 |
| 4 | 10.1 | 18.39 | 2.35 | 34.32 | 0 | 0 | 9.18 | 86 |
| 5 | 10.0 | 22.38 | 1.46 | 26.76 | 0 | 0.37 | 16.73 | 82 |
| 6 | 10.0 | 10.56 | 1.26 | 46.66 | 7.78 | 0.63 | 5.00 | 82 |
| 7 | 10.0 | 15.84 | 1.45 | 47.99 | 2.51 | 0.36 | 0 | 85 |

Ile: isoleucine
SA: salicylaldehyde
Tol: toluene

All the reaction products shown in Table 8 were analyzed proved to be completely epimerized.

We claim:

1. A process for preparing D-alloisoleucine comprising the steps of: combining (2S, 3S)-tartaric acid derivative of formula I:

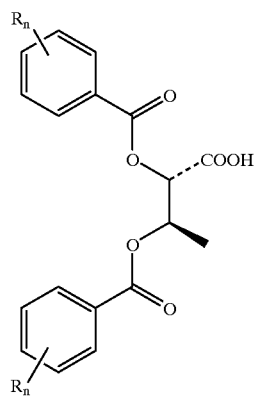

wherein R is a hydrogen atom, a $C_1$–$C_3$ lower alkyl group or lower alkoxy group, a chlorine atom, a bromine atom or a nitro group; and n is 0, 1 or 2; with an epimer mixture of L-isoleucine and D-alloisoleucine in a reaction medium to form a complex of D-alloisoleucine and the compound of formula I; separating the precipitated complex; and isolating D-alloisoleucine by decomposing the separated solid complex.

2. A process for preparing D-alloisoleucine according to claim 1, wherein the reaction of complex formation is carried out by using a tartaric acid derivative in which R in formula I is hydrogen atom or methyl group substituted at the p-position, and n is 1.

3. A process for preparing D-alloisoleucine according to claim 1, wherein the reaction is carried out by using water, a lower alcohol, or a mixture thereof as a reaction medium.

4. A process for preparing D-alloisoleucine according to claim 1, wherein the reaction is carried out by using 0.1 to 0.7 mole of the compound of formula I per 1 mole of the epimer mixture.

5. A process for preparing D-alloisoleucine according to claim 1, wherein the reaction is carried out by using 0.1 to 0.7 mole of the compound of formula I per 1 mole of the epimer mixture, and under addition of 0.05–0.7 equivalent of an inorganic acid.

6. A process for preparing D-alloisoleucine according to claim 1, wherein the complex formed from D-alloisoleucine and the compound of formula I is put in a lower alcohol to dissolve tartaric acid derivative, or the resolving agent, and to allow D-alloisoleucine to remain as a solid so that D-alloisoleucine may be isolated.

7. A process for preparing D-alloisoleucine according to claim 6, wherein isopropanol is used as the lower alcohol, to which 2–20 wt. % of water is added.

8. A complex consisting of D-alloisoleucine and the compound of formula I.

9. A process for isomerizing L-isoleucine, comprising the steps of: dispersing L-isoleucine in an inert solvent which does not substantially dissolve amino acids; isomerizing L-isoleucine in the presence of a lower fatty acid and an aliphatic or aromatic aldehyde; and obtaining the epimer mixture consisting of L-isoleucine and D-alloisoleucine precipitated from the solvent by solid-liquid separation.

10. A process for isomerizing L-isoleucine according to claim 9, wherein an aromatic hydrocarbon is used as the inert solvent which does not substantially dissolve amino acids.

11. A process for isomerizing L-isoleucine according to claim 10, wherein the aromatic hydrocarbon is selected from benzene, toluene, a xylene and a halogenated benzene.

12. A process for isomerizing L-isoleucine according to claim 9, wherein a $C_1$–$C_5$ saturated lower fatty acid is used as the lower fatty acid.

13. A process for isomerizing L-isoleucine according to claim 9, wherein benzaldehyde which is optionally substituted by hydroxyl group only or hydroxyl group and halogen atom is used as the aromatic aldehyde.

14. A process for isomerizing L-isoleucine according to claim 9, wherein 3–10 moles of the lower fatty acid is used per 1 mole of L-isoleucine.

15. A process for isomerizing L-isoleucine according to claim 9, wherein 0.01–0.3 mole of the aromatic aldehyde is used per 1 mole of L-isoleucine.

16. A process for preparing D-alloisoleucine comprising the steps of: suspending L-isoleucine in an inert solvent which does not substantially dissolve amino acids; isomerizing the L-isoleucine in the presence of a lower fatty acid and an aliphatic or aromatic aldehyde to an epimer mixture consisting of L-isoleucine and D-alloisoleucine; combining (2S,3S)-tartaric acid derivative of formula I:

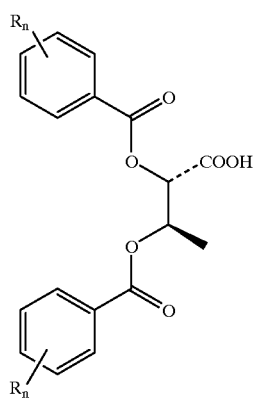

wherein R is hydrogen atom, a $C_1$–$C_3$ lower alkyl group or lower alkoxyl group, a chlorine atom, a bromine atom or a nitro group; and n is 0, 1 or 2; with the epimer mixture obtained in the former steps, to form a complex of D-alloisoleucine and the compound of formula I; separating the precipitated complex from the solution; and decomposing the separated complex to isolate D-alloisoleucine.

17. A process for preparing D-alloisoleucine according to claim 16, wherein a $C_1$–$C_5$ saturated lower fatty acid is used as the lower fatty acid, and benzaldehyde which is optionally substituted by hydroxyl group only or hydroxyl group and halogen atom is used as the aromatic aldehyde.

18. A process for preparing D-alloisoleucine according to claim 3, wherein the lower alcohol is methanol or ethanol.

19. A process for isomerizing L-isoleucine according to claim 12, wherein 3–10 moles of the lower fatty acid is used per 1 mole of L-isoleucine.

20. A process for isomerizing L-isoleucine according to claim 13, wherein 0.01–0.3 mole of the aromatic aldehyde is used per 1 mole of L-isoleucine.

* * * * *